United States Patent
Fattinger

(10) Patent No.: US 10,060,917 B2
(45) Date of Patent: Aug. 28, 2018

(54) DEVICE FOR USE IN THE DETECTION OF BINDING AFFINITIES

(71) Applicants: F. HOFFMANN-LA ROCHE AG, Basel (CH); HOFFMANN-LA ROCHE INC., Little Falls, NJ (US)

(72) Inventor: Christof Fattinger, Blauen (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 324 days.

(21) Appl. No.: 14/904,039

(22) PCT Filed: Jul. 11, 2014

(86) PCT No.: PCT/EP2014/064884
§ 371 (c)(1),
(2) Date: Jan. 8, 2016

(87) PCT Pub. No.: WO2015/004264
PCT Pub. Date: Jan. 15, 2015

(65) Prior Publication Data
US 2016/0161477 A1 Jun. 9, 2016

(30) Foreign Application Priority Data
Jul. 12, 2013 (EP) .................................. 13176362

(51) Int. Cl.
*G01N 33/551* (2006.01)
*G01N 33/543* (2006.01)
*G01N 21/77* (2006.01)

(52) U.S. Cl.
CPC ... *G01N 33/54386* (2013.01); *G01N 21/7743* (2013.01); *G01N 33/54373* (2013.01)

(58) Field of Classification Search
USPC ....................................................... 422/82.11
See application file for complete search history.

(56) References Cited

U.S. PATENT DOCUMENTS

| 5,071,248 A | 12/1991 | Tiefenthaler et al. |
| 5,081,012 A | 1/1992 | Flanagan et al. |

(Continued)

FOREIGN PATENT DOCUMENTS

| CN | 101368912 A | 2/2009 |
| CN | 101368912 B | 2/2009 |

(Continued)

OTHER PUBLICATIONS

International Search Report and Written Opinion issued in PCT/EP2014/064884 dated Oct. 6, 2014.

(Continued)

*Primary Examiner* — Chris L Chin
(74) *Attorney, Agent, or Firm* — Mintz Levin Cohn Ferris Glovsky and Popeo, P.C.

(57) ABSTRACT

A device (1) for use in the detection of binding affinities comprises a planar waveguide (2) arranged on a substrate (22). The waveguide (2) has an outer surface (21) and a plurality of incoupling lines (31) for coupling a beam of coherent light into the waveguide (2) such that a parallel beam of coherent light (62) propagates along the waveguide (2). The incoupling lines (31) are curved and have an increasing distance between adjacent incoupling lines (31). A divergent beam of coherent light (61) of a predetermined wavelength is coupled into the waveguide (2) such that it propagates along the waveguide (2). A plurality of binding sites (51) is attached to the outer surface (21) along at least one further plurality of diffraction lines arranged in an outcoupling section of the waveguide (2). These diffraction lines comprise a plurality of curved outcoupling lines (41) having a decreasing distance between adjacent outcoupling lines. They decouple a diffracted portion of coherent light from the planar waveguide (2), and the decoupled portion of (Continued)

coherent light (63) converges into a predetermined second focal location (631).

12 Claims, 5 Drawing Sheets

(56) References Cited

U.S. PATENT DOCUMENTS

| | | | | |
|---|---|---|---|---|
| 5,082,629 | A * | 1/1992 | Burgess, Jr. | G01N 21/552 356/128 |
| 6,312,961 | B1 * | 11/2001 | Voirin | G01N 21/648 356/317 |
| 6,429,022 | B1 * | 8/2002 | Kunz | G01N 21/7743 422/82.11 |
| 2008/0298740 | A1 * | 12/2008 | Hlousek | G01N 21/7743 385/12 |

FOREIGN PATENT DOCUMENTS

| | | |
|---|---|---|
| EP | 1085315 A1 | 3/2001 |
| WO | WO-93/01487 A1 | 1/1993 |

OTHER PUBLICATIONS

Pawlak et al. Zeptosens' protein microarrays, Proteomics 2002, 2, 383-393.
Kumar et al. "Light focusing by chrped waveguide grating coupler." XP060015129.

* cited by examiner

DEVICE FOR USE IN THE DETECTION OF BINDING AFFINITIES

CROSS-REFERENCE TO RELATED APPLICATIONS

This application is a national stage application, filed under 35 U.S.C. § 371, of International Application No. PCT/EP2014/064884 filed on Jul. 11, 2014, which claims priority to European Patent Application No. 13176362.5 filed on Jul. 12, 2013, the contents of each of which are hereby fully incorporated by reference.

FIELD

The present invention relates to a device for use in the detection of binding affinities as well as to a method in accordance with the respective independent claim.

BACKGROUND

Such devices are used, for example, as biosensors in a large variety of applications. One particular application is the detection or monitoring of binding affinities or processes. For example, with the aid of such biosensors various assays detecting the binding of target samples to binding sites can be performed. Typically, large numbers of such assays are performed on a biosensor at spots which are arranged in a two-dimensional microarray on the surface of the biosensor. The use of microarrays provides a tool for the simultaneous detection of the binding affinities or processes of different target samples in high-throughput screenings. For detecting the affinities of target samples to bind to specific binding sites, for example, the affinity of target molecules to bind to specific capture molecules, a large number of capture molecules are immobilised on the outer surface of the biosensor at individual spots (e.g. by ink-jet spotting or photolithography). Each spot forms an individual measurement zone for a predetermined type of capture molecule. The binding of a target molecule to a specific type of capture molecule is detected and is used to provide information on the binding affinity of the target molecule with respect to the specific capture molecule.

A known technique for detecting binding affinities of target samples utilizes fluorescent labels. The fluorescent labels are capable of emitting fluorescent light upon excitation. The emitted fluorescent light has a characteristic emission spectrum which identifies the present fluorescent label at a particular spot. The identified fluorescent label indicates that the labelled target molecule has bound to the particular type of binding sites present at this spot.

A sensor for detecting labelled target samples is described in the article "Zeptosens' protein microarrays: A novel high performance microarray platform for low abundance protein analysis", Proteomics 2002, 2, S. 383-393, Wiley-VCH Verlag GmbH, 69451 Weinheim, Germany. The sensor described there comprises a planar waveguide arranged on a substrate. The planar waveguide has an outer surface capable of attaching a plurality of binding sites thereon. Moreover, the planar waveguide has a plurality of incoupling lines for coupling a beam of coherent light into the planar waveguide in a manner such that a beam of coherent light propagates along the planar waveguide. The coherent light propagates through the planar waveguide under total reflection with an evanescent field of the coherent light propagating along the outer surface of the planar waveguide. The depth of penetration of the evanescent field into the medium of lower refractive index at the outer surface of the planar waveguide is in the order of magnitude of a fraction of the wavelength of the coherent light propagating through the planar waveguide. The evanescent field excites the fluorescent labels of the labelled target samples bound to the binding sites arranged on the surface of the planar waveguide. Due to the very small depth of penetration of the evanescent field into the optically thinner medium at the outer surface of the planar waveguide, only the labelled samples bound to the binding sites immobilized on the outer surface of the planar waveguide are excited. The fluorescent light emitted by these labels is then detected with the aid of a CCD camera.

While it is principally possible to detect the binding affinities using fluorescent labels, this technique is disadvantageous in that the detected signal is produced by the fluorescent labels rather than by the binding partners themselves. In addition, labelling the target samples requires additional preparation steps. Moreover, labelled target samples are comparatively expensive. Another disadvantage is the falsification of the results caused by steric hindrance of the fluorescent labels at the target sample which might interfere with the binding of the target samples to the capture molecules. Further disadvantages are the falsification of the results due to photobleaching of the labels or quenching effects.

SUMMARY

It is an object of the present invention to provide a device for use in the detection of binding affinities between a target sample and a binding site as well as a method capable of providing a signal representative for the binding affinities which overcome or at least greatly reduce the disadvantages of the prior art described above.

In accordance with the invention, this object is achieved by a device for use in the detection of binding affinities. The device comprises a planar waveguide arranged on a substrate. The planar waveguide has an outer surface and a plurality of incoupling lines for coupling a beam of coherent light into the planar waveguide in a manner such that in operation a parallel beam of coherent light propagates along the planar waveguide with an evanescent field propagating along the outer surface thereof. The plurality of incoupling lines are curved and arranged to have an increasing distance between adjacent incoupling lines when viewed in the direction of propagation of the parallel beam of coherent light along the planar waveguide, the arrangement of the plurality of incoupling lines and the distance between adjacent incoupling lines being such that in operation a divergent beam of coherent light of a predetermined wavelength coming from a predetermined first focal location and impinging on the plurality of incoupling lines is coupled into the planar waveguide in a manner such that the parallel beam of coherent light propagates along the planar waveguide. A plurality of binding sites capable of binding a target sample is attached to the outer surface. The attached binding sites are arranged along at least one further plurality of diffraction lines arranged in an outcoupling section of the planar waveguide. The at least one further plurality of diffraction lines comprises a plurality of curved outcoupling lines which are arranged to have a decreasing distance between adjacent curved outcoupling lines when viewed in the direction of propagation of the coherent light impinging thereon so as to be capable of diffracting a portion of the coherent light of the predetermined wavelength to decouple it from the planar waveguide in a manner such that the decoupled portion of coherent light of the predetermined wavelength converges into a predetermined second focal location to provide at the second focal location a signal representative of the binding affinity between the binding sites and the target sample.

It is to be noted that the term "curved outcoupling lines" comprises both, "real" lines having an optically diffracting effect (physically present lines, e.g. the lines of an optical grating) and diffracting a portion of the coherent light of the predetermined wavelength to the predetermined second focal location (in this case the binding sites are arranged along a further plurality of "virtual" lines to form a biological grating together with the target samples, in order to diffract a portion of the parallel beam of coherent light towards the "real" lines), as well as "virtual" lines (lines which may not be physically present on the outer surface of the waveguide or which themselves do not have an optically diffracting effect but are formed by the binding sites arranged along these "virtual" lines to form a biological grating together with the target sample). Both types of "curved outcoupling lines", the "real" lines as well as the "virtual" lines diffract a portion of the coherent light of the predetermined wavelength to the predetermined second focal location. In the latter case, i.e. when the curved outcoupling lines are formed by the "virtual" lines of the biological grating, "real" lines such as those of an optical grating may or may not be present in addition to the biological grating.

The term "curved incoupling lines" also comprises both "real" lines having an optically diffracting effect (physically present lines, e.g. the lines of an optical grating) and diffracting a portion of the coherent light of the predetermined wavelength to couple the diffracted portion of coherent light into the planar waveguide as well as "virtual" lines (lines which may not be physically present on the outer surface of the waveguide or which themselves do not have an optically diffracting effect but are formed by binding sites arranged along these "virtual" lines to form a biological grating together with the target sample). The "real" lines may for example be embodied as curved physical lines which couple a divergent beam of coherent light into the waveguide, whereas "virtual" lines may be curved lines which couple a divergent beam of coherent light into the planar waveguide, with binding sites being arranged along these virtual lines to diffract (together with the target sample bound thereto) a portion of a divergent beam of coherent light coming from a point light source (arranged at a predetermined location) and to couple the diffracted portion of the coherent light into the planar waveguide. The curved incoupling lines ("real" lines or "virtual" lines) have an increasing distance from one another when viewed in the direction of propagation of the coherent light coupled into the planar waveguide. It is thus possible, that both the incoupling lines and the outcoupling lines may comprise only biological gratings (no "real" lines). This may be advantageous with regard to the manufacture of such gratings, since manufacture of both the incoupling lines and the outcoupling lines can then be performed in a single step using lithography techniques. This may lead to less expensive manufacture of the gratings.

In operation, coherent light which has been diffracted in the outcoupling section at attached binding sites bound to the applied target sample (together forming the biological grating) can be provided at the second focal location as a measure for the binding affinity. For example, the intensity of the coherent light provided at the predetermined second focal location is detected and compared to a known intensity of coherent light which has been diffracted by the binding sites only (without having applied the target sample). The change in intensity is representative of (i.e. is a measure for) the binding affinity between the binding sites and the target sample since the intensity at the predetermined second focal location is significantly different as target sample has bound to the binding sites when compared to the intensity at the predetermined second focal location caused by the binding sites only. This overcomes the need for labelling the target samples since the outcoupled portion of the coherent light constructively interferes at the predetermined second focal location to provide a detectable signal. "Constructively interferes at the predetermined second focal location" means in other words that the coherent light converging into the predetermined second focal location at the said predetermined second focal location has a difference in optical path length which is an integer multiple of the predetermined wavelength. This interference maximum at the predetermined second focal location provides a detectable signal originating from the binding sites bound to the target sample.

In general, "binding sites" are locations on the outer surface of the planar waveguide to which a target sample may bind (or binds in case of binding affinity). The detection of binding affinities according to the invention is neither limited to specific types of target samples nor to any type of binding sites, but rather the binding characteristics of e.g. molecules, proteins, DNA etc. as target samples can be analysed with respect to any suitable type of binding sites on the planar waveguide. Technically, the term "diffracted" denotes the interference of the coherent light of the evanescent field which already has interacted with target samples bound to the binding sites. The term diffracted "portion" refers to the fact, that not the entire light is diffracted for decoupling from the waveguide so that a portion (in fact the main portion) of the parallel beam of coherent light continues to propagate along the planar waveguide. The term "parallel beam" explicitly includes some deviations according to which the light propagates in a converging or diverging manner in the waveguide. The extent of those deviations is limited by the intensity of the detected signal so that parallel includes deviations which allow for providing at the second focal location a signal representative of the binding affinity between the binding sites and the target sample. Because of the reversibility of the optical path of the coherent light, the roles of the incoupling lines and the outcoupling lines can be generally exchanged, resulting in analoguous functions of the embodiments described in the invention. The binding sites may be arranged at more than one plurality of lines. The arrangement of the binding sites along the lines represents the optimum case in which all binding sites are exactly arranged on the ideal line. The optimum arrangement of the binding sites is associated with a maximum signal at the second focal location, but in practice, the arrangement of the binding sites will deviate to some extent from such optimum arrangement while the decoupled portion of the parallel beam of coherent light converging into the second focal location is still present. The plurality of incoupling lines and the plurality of curved outcoupling lines are arranged on the outer surface of the planar waveguide in a manner such that their locations in $x_j, y_j$-coordinates are geometrically defined by the equation $$x_j = \frac{\lambda N(A_0 + j) - \sqrt{n_s^2(N^2 - n_s^2)(y_j^2 + f^2) + (n_s \lambda)^2 (A_0 + j)^2}}{N^2 - n_s^2}$$

wherein

λ is the vacuum wavelength of the propagating light,

N is the effective refractive index of the guided mode in the planar waveguide; N depends on the thickness and the refractive index of the planar waveguide, the refractive index of the substrate, the refractive index of a medium on the outer surface of the planar waveguide and the polarization of the guided mode, $n_s$ is the refractive index of the substrate, f is the distance (focal length) between the focal location and the outer surface of the planar waveguide, $A_0$ is an integer which is chosen to be close to $n_s f/\lambda$, and j is a running integer that indicates the index of the respective line.

The chosen integer $A_0$ assigns negative x-values at the centre of the lines to negative j values and positive x-values at the centre of the lines with positive j values. Or to say it in other words, the integer $A_0$ defines the origin of the x,y-coordinates frame that is used for the location of the lines at the outer surface of the planar waveguide; the chosen $A_0$ value allocates the detection location at x=0, y=0, z=−f.

The first focal location and the second focal location are in a preferred example of a diameter of approximately 0.5 μm and are arranged at a distance of between 10-200 μm.

According to one aspect, the plurality of incoupling lines is arranged at a first surface portion of the outer surface of the planar waveguide and the plurality of curved outcoupling lines is arranged at a second surface portion of the outer surface of the planar waveguide. The first surface portion includes a blank section in which there are no lines and the second surface portion includes a further blank section in which there are no lines. The blank section is formed to avoid a $2^{nd}$ order Bragg reflection (an interference maximum of coherent light diffracted at the respective plurality of lines which emerges in the planar waveguide), or similar optical effects, which potentially impair the overall intensity of the detected signal. Preferably, the first surface portion and the second surface portion are of a diameter of 25-300 μm.

According to another aspect, the first surface portion and the second surface portion are arranged spatially separated at the outer surface of the planar waveguide. The spatially separated arrangement allows for diffracting a maximal portion of the evanescent field of the parallel beam of coherent light (incoupled by all lines of the plurality of incoupling lines) at every line of the plurality of curved outcoupling lines.

According to an alternative aspect, the first surface portion and the second surface portion are arranged at the outer surface of the planar waveguide to at least partially overlap in a manner such that the blank section and the further blank section form a common blank section. In the at least partially overlapping arrangement, a minimal area of the outer surface of the planar waveguide is covered by said first and second surface portions. The reduced size of the covered area allows to arrange a higher number of such first and second surface portions at the outer surface of the planar waveguide.

According to a further aspect, the first surface portion and the second surface portion are of the same size.

According to an alternative aspect, the at least one further plurality of diffraction lines arranged in the outcoupling section further comprises a plurality of straight lines. The straight lines run parallel to one another with a constant distance between adjacent straight lines and are arranged at an angle β relative to the direction of propagation of the parallel beam of coherent light in a manner such that a portion of the parallel beam of coherent light is diffracted under a diffraction angle α relative to the straight lines such that the diffracted portion of the parallel beam of coherent light impinges onto the plurality of curved outcoupling lines. The attached binding sites are arranged along the plurality of straight lines or along the plurality of curved outcoupling lines.

The direction of propagation of the parallel beam of coherent light is defined as starting from the plurality of incoupling lines and extending in the direction in which the coherent light is coupled into the planar waveguide which is usually close to a direction perpendicular to the plurality of incoupling lines. The coherent light diffracted at the binding sites bound to target samples impinges onto the plurality of curved outcoupling lines of the second surface portion under the diffraction angle α relative to the straight lines. Under the diffraction angle α, the light coming from the plurality of straight lines constructively interferes (i.e. light diffracted at different straight lines has a difference in optical path length of an integer multiple of the predetermined wavelength) at the plurality of curved outcoupling lines. The diffraction angle α depends on the constant distance between adjacent predetermined straight lines taking into account the predetermined wavelength and the refractive indices of the substrate, of the planar waveguide and of the medium at the outer surface (e.g. the medium at the outer surface may comprise the target samples) of the planar waveguide.

According to one aspect, the plurality of curved outcoupling lines is arranged at the outer surface in a partition of the planar waveguide through which the portion of the parallel beam of coherent light diffracted at the straight lines propagates, and through which no other light of the parallel beam of coherent light propagates. This allows to detect the light at the second focal location with a reduced background signal because the second focal location is located normal to an area of the outer surface of the planar waveguide through which no other "non-diffracted" light of the parallel beam of coherent light propagates.

According to another aspect, a surface coating layer is arranged on top of the outer surface of the planar waveguide. The surface coating layer has a porous internal structure to allow the target sample applied to the coating layer to diffuse therethrough to reach the binding sites attached to the outer surface of the planar waveguide. Advantageously, the target sample can be applied in a mixture comprising other compounds as well but only the target sample is capable of diffusing through the porous internal structure of the coating layer to reach the outer surface of the planar waveguide.

In another aspect, the invention relates to a method for the detection of binding affinities, the method comprising the steps of:

providing a device as described herein, applying to the outcoupling section of the planar waveguide along the at least one further plurality of diffraction lines where the binding sites are arranged a target sample for which the binding affinity between the binding sites and the target sample is to be detected, generating at the predetermined first focal location a divergent beam of coherent light in a manner so as to impinge on the plurality of incoupling lines of the planar waveguide to couple the divergent beam of coherent light into the planar waveguide in a manner such that the beam of coherent light coupled into the planar waveguide propagates as a parallel beam of coherent light along the planar waveguide with an evanescent field of the parallel beam of coherent light propagating along the outer surface thereof, wherein a portion of the coherent light is diffracted by the plurality of curved outcoupling lines of the outcoupling section of the planar waveguide to decouple it from the planar waveguide in a manner such that the decoupled portion of the coherent light converges into the second predetermined focal location, and detecting the decoupled portion of coherent light at the second predetermined focal location as a signal representative of the binding affinity between the binding sites and the target sample.

According to an aspect of the method, the decoupled portion of the parallel beam of coherent light is detected in a detection zone having a predetermined size and being arranged to include the second predetermined focal location to determine that location in the detection zone, where the decoupled portion of coherent light of the predetermined wavelength has a relative maximum intensity. The location of the relative maximum intensity is defined as the second predetermined focal location. The relative maximum intensity allows to find the detectable signal in the detection zone. The size of the detection zone depends on the manufacturing tolerances of the planar waveguide having a typical thickness in the range of 100 nm to 300 nm; a typical manufacturing tolerance of the waveguide thickness is a few nanometers. This tolerance corresponds to a lateral extension of the detection zone in the order of a few percent of the lateral extension of the outcoupling section.

According to another aspect of the method, the divergent beam of coherent light is successively generated at different locations in a beam generation zone having a predetermined size and being arranged to include the first predetermined focal location. For each successively generated beam of coherent light that location in the detection zone having the relative maximum intensity of the decoupled portion of the parallel beam of coherent light is determined, defining that location in the detection zone where the relative maximum intensity is highest as the second predetermined focal location, and defining that location in the beam generation zone, where the corresponding beam is generated as the first predetermined focal location. Advantageously, defining the first predetermined focal location for which the relative maximum intensity is highest allows to find the absolute maximum intensity as the best detectable signal at the second predetermined focal location. This is of advantage because different planar waveguides usually have a different thickness, e.g. in case of manufacturing tolerances, which may lead to different locations of the first and second predetermined focal locations for each device. The exact location of both predetermined focal locations can be found in this manner. The size of the beam generation zone and of the detection zone depends on the magnitude of manufacturing tolerances.

In the following two preferred alternative embodiments of the method according to the invention are explained. Both embodiments relate to the detection of binding affinities by using the first, respectively, the second embodiment of the device showing manufacturing tolerances.

In the first alternative of the method, the beam generation zone is an area in a first plane parallel to the outer surface of the planar waveguide. The detection zone is a straight line extending parallel to the direction of propagation of the parallel beam of coherent light in a second plane parallel to the outer surface of the planar waveguide. This allows to detect binding affinities by using a device according to the first embodiment. The working principle and the advantages thereof are discussed in detail below with reference to FIG. 7 so as to avoid unnecessary iteration here.

In the second alternative of the method, the beam generation zone is an area in a first plane parallel to the outer surface of the planar waveguide. The detection zone is an area in a second plane parallel to the outer surface of the planar waveguide. This allows for detecting the decoupled portion of the parallel beam of coherent light at the second predetermined focal location of a device according to the second embodiment in which the outcoupling section additionally comprises a plurality of straight lines. The working principle and advantages are explained in detail with reference to FIG. 8 so as to avoid unnecessary iteration here.

BRIEF DESCRIPTION OF THE DRAWINGS

Further advantageous aspects of the invention become apparent from the following description of embodiments of the invention with reference to the accompanying drawings in which.

DETAILED DESCRIPTION

Figure 1:
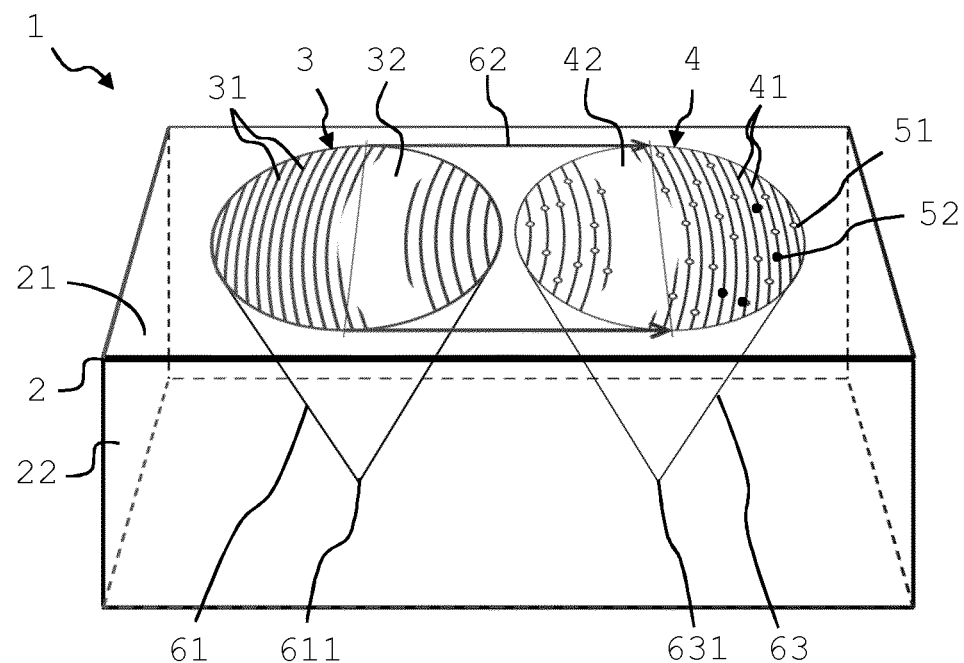
FIG. 1 shows a perspective view of a device according to a first embodiment of the invention with a first surface portion and a second surface portion arranged spatially separated at an outer surface of the planar waveguide.

A first embodiment of the device 1 according to the invention is shown in FIG. 1 in a perspective view. A planar waveguide 2 is arranged on top of a substrate 22 and comprises an outer surface 21 at the upper side thereof. Outer surface 21 of the planar waveguide comprises a plurality of incoupling lines 31 arranged in a first surface portion 3 and a plurality of curved outcoupling lines 41 arranged in a second surface portion 4. The plurality of curved outcoupling lines 41 comprise binding sites 51 to some of which a target sample 52 has bound.

The plurality of incoupling lines 31 are curved and arranged to have an increasing distance between adjacent incoupling lines 31 (from left to right). The curvature and the increasing distance between adjacent lines is chosen to allow for coupling a divergent beam of coherent light 61 coming from a first focal location 611 into the planar waveguide, with the first focal location 611 being arranged in the shown example at the lower side of the substrate 22. The generation of such divergent beam of coherent light 61 is explained for the system described below with reference to FIG. 6. The divergent beam of coherent light 61 (or a portion thereof) is coupled into the planar waveguide 2 by the plurality of incoupling lines 31 which act as an optical grating having a plurality of grating lines (e.g. grooves, elongated protrusions, periodical changes of a refractive index of the planar waveguide). The coupling of divergent beam of coherent light 61 into the planar waveguide 2 causes the parallel beam of coherent light 62 to propagate along the planar waveguide 2, with a portion of the parallel beam of coherent light 62 propagating along the outer surface 21 to form an evanescent field (not shown) in the proximity of the outer surface 21 of the planar waveguide 2.

As already mentioned, the plurality of curved outcoupling lines 41 comprises binding sites 51 attached to the outer surface 21 of the planar waveguide 2. Some of the attached binding sites 51 are bound to target sample 52 applied to outer surface 21 of the planar waveguide 2. The curvature of the plurality of curved outcoupling lines 41 as well as the arrangement of the adjacent incoupling lines having a decreasing distance between adjacent incoupling lines 31 from left to right is chosen to allow for decoupling the parallel beam of coherent light 62 such that a decoupled portion of the parallel beam of coherent light 63 converges into a second focal location 631. Second focal location 631 is arranged at the lower side of substrate 22. Since the intensity of the outcoupled portion of the parallel beam of coherent light 63 converging into second focal location 631 changes in case of binding sites 51 are bound to target samples 52, a signal (intensity) representative to the binding affinity between binding sites 51 and target sample 52 is provided therein.

As shown, first surface portion 3 includes a blank section 32 and second surface portion 4 includes a further blank section 42, each of which forms a surface area free of any lines. Blank section 32 and further blank section 42 are completely spatially separated. An alternative arrangement is discussed in the following.

Figure 2:
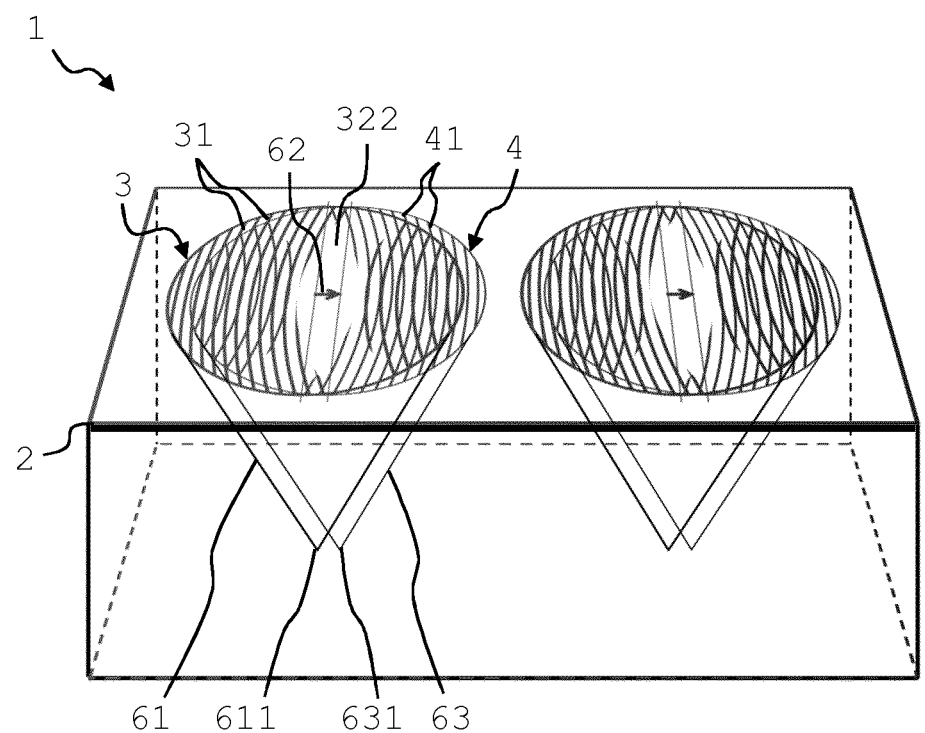
FIG. 2 shows a perspective view of a device according to a second embodiment of the invention with the first surface portion and the second surface portion arranged at the outer surface of the planar waveguide in a manner so as to at least partially overlap.

The alternative arrangement is shown in FIG. 2, blank section 32 and further blank section 42 form a common blank section 322. First surface portion 3 and second surface portion 4 are arranged in an overlapping manner in which the plurality of incoupling lines 31 overlap with the plurality of curved outcoupling lines 41 such that blank section 32 and further blank section 42 "overlap" to form common blank section 322.

In use, the divergent beam of coherent light 61 is coupled into the planar waveguide 2 by the plurality of incoupling lines 31 so that a parallel beam of coherent light 62 propagates along planar waveguide 2 with an evanescent field propagating along the outer surface 21 thereof. A portion of the evanescent field (and thus of the beam) is diffracted at the binding sites (not shown) bound to target samples (not shown) which are arranged along the plurality of curved outcoupling lines 41. A portion of the parallel beam of coherent light 62 is thus decoupled from the planar waveguide 2 in a manner such that the outcoupled portion of parallel beam of coherent light 63 converges into the second focal location 631. In principle, the coherent light of the evanescent field is diffracted at binding sites bound to target samples so that light diffracted at the binding sites bound to target samples arranged along each of the plurality of curved outcoupling lines 41 constructively interferes at the second focal location 631. First focal location 611 and the adjacent second focal location 631 are separated by a distance of 10 μm-20 μm.

Figure 3:
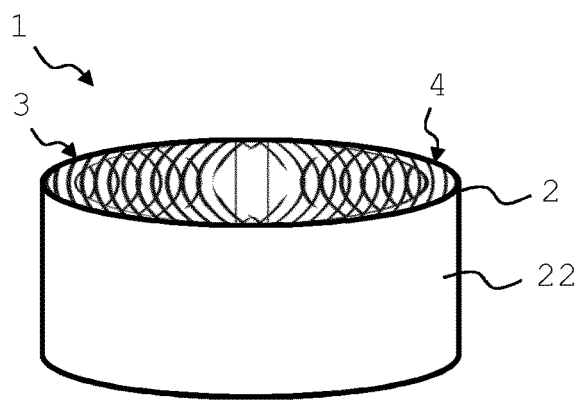
FIG. 3 shows a perspective view of the device of FIG. 2 with a substrate having approximately the size of the first surface portion overlapping with the second surface portion.

FIG. 3 illustrates device 1 having substrate 22 and planar waveguide 2 arranged thereon, and having a diameter which corresponds to the size of the first surface portion 3 overlapping with the second surface portion 4. Hence, a compact device 1 is provided having an outer contour of a very small diameter, in particular in the range of 25 μm to 500 μm, and preferably 300 μm.

Figure 4:
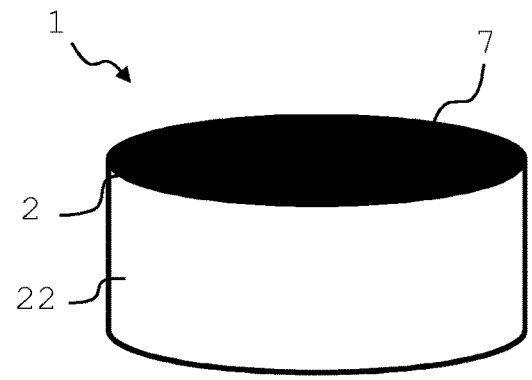
FIG. 4 shows a perspective view of the device of FIG. 3 with a surface coating layer.

FIG. 4 illustrates the device 1 according to another advantageous aspect in which a surface coating layer 7 is formed on top of the outer surface of the planar waveguide 2 arranged on substrate 22. Surface coating layer 7, in the present example, is made of a hydrogel that is covered by a light absorbing (black) membrane with nanopores. These materials have a porous internal structure having a predetermined porosity in the range of 5% to 90% (fraction of the volume of pores relative to the total volume) and a predetermined pore size in the range of 10 nm to 10 μm (average diameter of pores). This allows the applied target sample (e.g. a specific type of molecule) to diffuse therethrough to reach the binding sites attached to the outer surface.

Figure 5:
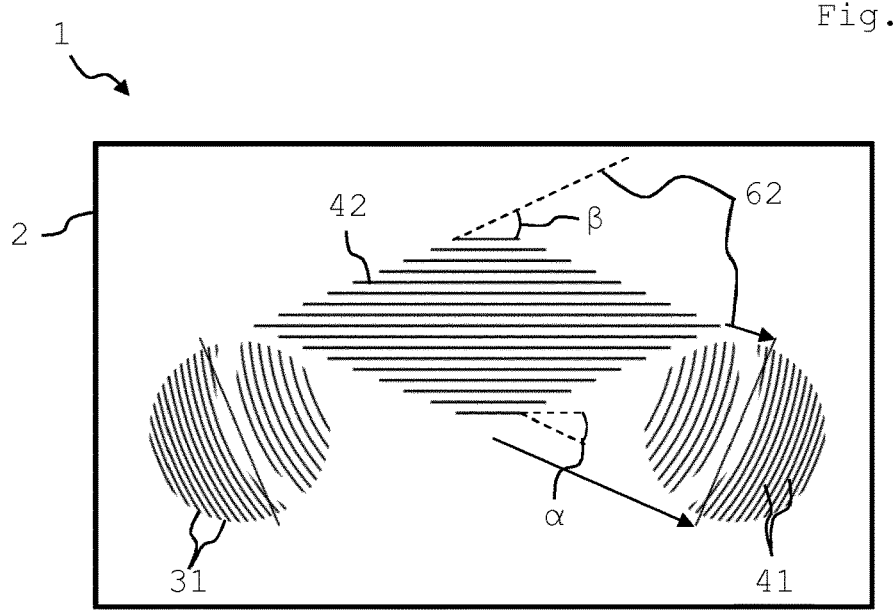
FIG. 5 shows a perspective view of a device according to a third embodiment of the invention with the outcoupling section further comprising a plurality of straight lines.

Another embodiment of the device 1 is depicted in FIG. 5 in a top view. At the left hand side, the plurality of incoupling lines 31 and at the right side the plurality of curved outcoupling lines 41 are arranged. Different from the previously described embodiments, the outcoupling section additionally comprises a plurality of straight lines 42 which are arranged between the incoupling lines 31 and the outcoupling lines 41. In the present example, the binding sites (not shown) are arranged along the plurality of straight lines 42. The straight lines 42 are arranged to run parallel to one another with a constant distance between adjacent straight lines. The divergent beam of coherent light (not shown) is coupled into the planar waveguide 2 by the plurality of incoupling lines 31 so that a beam of coherent light 62 (the beam of coherent light is shown in dashed lines and the diffracted portion of the beam of coherent light is shown as parallel arrows) propagates as a parallel beam along planar waveguide 2 together with its associated evanescent field. The individual lines of the plurality of straight lines 42 are arranged at an angle β with respect to the propagation direction of the parallel beam of coherent light 62. The binding sites bound to the target samples which are arranged along the plurality of straight lines 42 diffract a portion of the evanescent field (and thus of the parallel beam of coherent light), and this diffracted portion of the beam of coherent light 62 propagates along the planar waveguide 2 towards the plurality of curved outcoupling lines 41. The portion of the parallel beam of coherent light 62 is diffracted under a diffraction angle α (which equals β) relative to the straight lines. The intensity of the diffracted portion of the parallel beam of coherent light 62 which impinges onto the plurality of curved outcoupling lines and of which a portion is decoupled from the planar waveguide 2 provides a signal representative of the binding affinity, as described already for the first embodiment.

Figure 6:
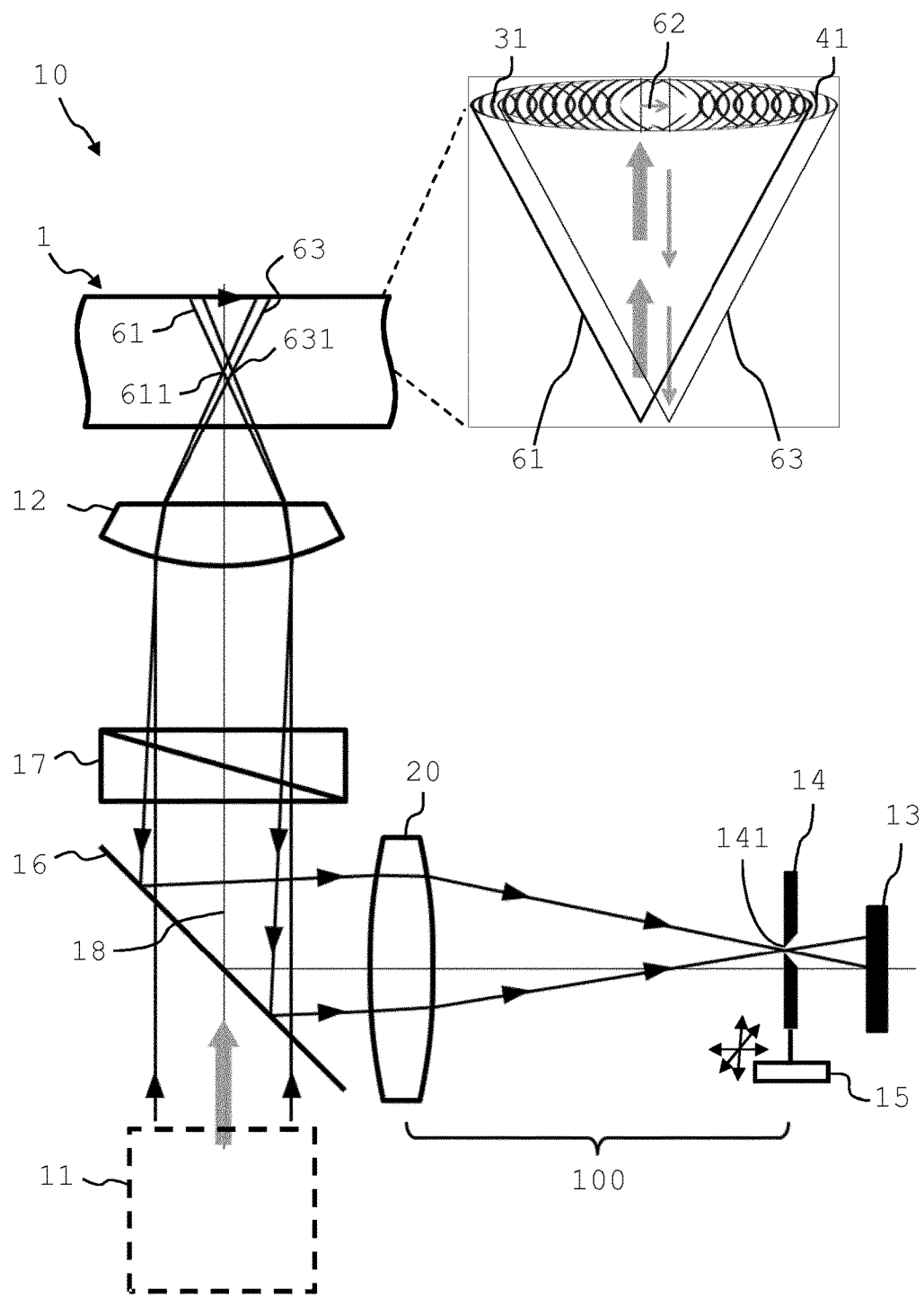
FIG. 6 shows a first embodiment of a system for using a device for use in the detection of binding affinities.

FIG. 6 shows a system 10 for detecting binding affinities. System 10 comprises a laser light source 11 which is capable of providing at first focal location 611 of a device 1 (as described above) a divergent beam of coherent light 61. Laser light source 11 generates a beam of coherent light which is focussed by focussing lens 12 into first focal location 611. An optical scanning unit 12, 17 comprises a scanner 17 and a focussing lens 12 and generates a divergent beam of coherent light 61 in a beam generation zone (as is explained with reference to FIGS. 7 and 8). Divergent beam of coherent light 61 coming from the first focal location 611 is coupled into the planar waveguide 2 and generates a decoupled portion 63 of diffracted coherent light which converges into second focal location 631. System 10 further comprises an optical detection unit providing a spatial filter 100 capable of detecting the intensity of the converging beam of the decoupled portion 63 of diffracted coherent light by means of an optical detector 13 arranged behind a diaphragm 14 (when viewed in the direction of the path of the light). Optical detector 13 extends perpendicular to the optical axis 18. The diaphragm 14 is arranged on a movable positioning support 15. Diaphragm 14 is movable parallel to the extension of the optical detector 13 to a position in which any light other than the light coming from the second focal location 631 is masked out, so that only light from second focal location 631 impinges onto the optical detector 13 through an opening 141 in diaphragm 14. The diaphragm 14 arranged on the movable positioning support 15 allows for detection of the decoupled portion 63 of the diffracted coherent light at different locations which are arranged at different positions relative to the plurality of curved outcoupling lines 41 in a plane parallel to the outer surface of the planar waveguide (i.e. in the detection zone).

In other words, a system 10 for using the device 1 as described above (i.e. according to anyone of the device claims) in the detection of binding affinities comprises a light source 11 and an optical scanning unit 12, 17 capable of generating a divergent beam of light at the first focal location 611 of a device 1 according to anyone of the device claims to allow for providing a decoupled portion 63 of diffracted coherent light converging into the second focal location 631, and an optical detection unit 13, 14, 16, 20 capable of detecting the intensity of the converging beam of the decoupled portion 63 of diffracted coherent light. The optical detection unit 13, 14, 16, 20 comprises an optical detector 13 arranged behind a diaphragm 14 having an opening 141. The optical detection unit 13, 14, 16, 20 further comprises a beam splitter 16, a second focussing lens 20 and a movable positioning support 15 for the diaphragm 14. The converging beam (decoupled portion 63) of diffracted coherent light is transmitted by the focussing lens 12, the scanner 17, the beam splitter 16 and the second focussing lens 20 to impinge onto the diaphragm 14. By moving the diaphragm 14 arranged on the movable positioning support 15 in a plane perpendicular to the optical axis, the opening 141 in the diaphragm 14 can be positioned at the optically conjugate position to second focal location 631 of the decoupled portion 63 (converging beam) of diffracted coherent light. At that position of the diaphragm 14, the decoupled portion 63 of diffracted coherent light (converging beam) passes through the opening 141 in the diaphragm 14 and impinges on the detector 13 where its intensity is measured by means of the optical detector 13.

Advantageously, the system 10 further comprises the device 1 as described above.

Figure 7:
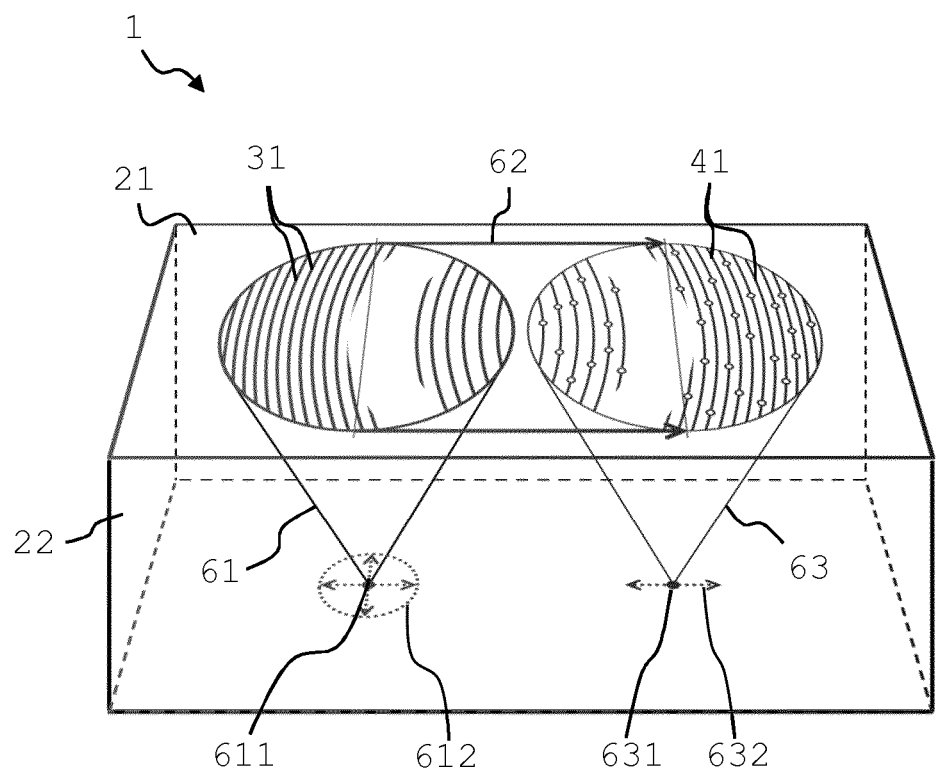
FIG. 7 shows the device of FIG. 1 with different first focal locations arranged in a beam generation zone and different second focal locations arranged in a detection zone forming a straight line in the plane parallel to the outer surface of the planar waveguide.
Figure 8:
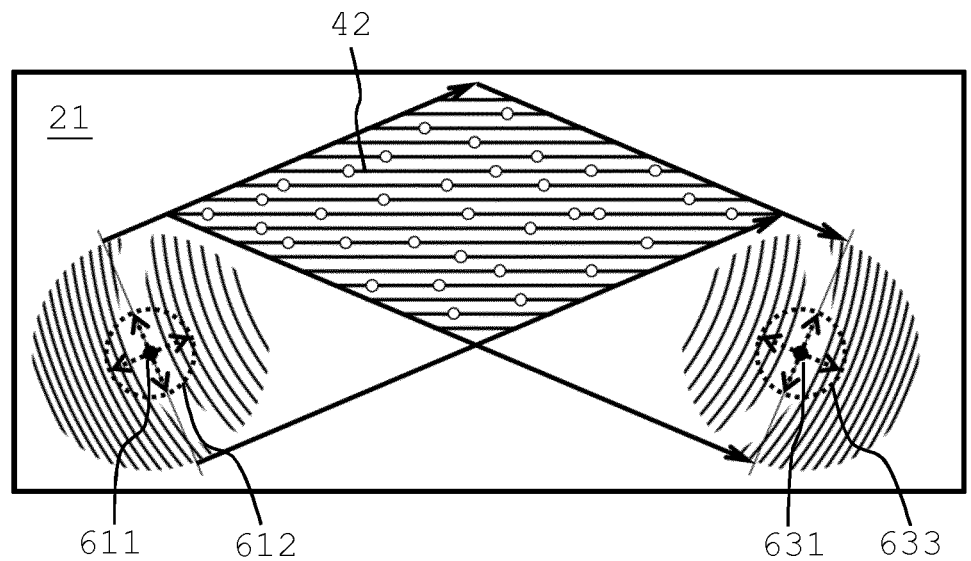
FIG. 8 shows the device of FIG. 5 with different first focal locations arranged in a beam generation zone and different second focal locations arranged in a detection zone forming an area in the plane parallel to the outer surface of the planar waveguide.

FIG. 7 and FIG. 8 are explained together in the following because they both refer to the same technical aspect of generating a divergent beam of coherent light 61 in a beam generation zone 612, and of detecting the decoupled portion 63 of the beam of diffracted coherent light converging into the second focal location 631 in a detection zone 632. This allows to detect a signal at the second focal location 631 even with devices 1 having structural deviations caused by the production of such a device 1 (e.g. variations in the thickness of the planar waveguide in the range of typical manufacturing tolerances). In other words, it allows for the detection of binding affinities in a device 1 in which the location of the first and second focal locations are not absolutely precisely known.

Referring to FIG. 7, a method for detecting the signal of highest intensity in the detection zone 632 of the second focal location 631 will be described for a device 1 according to the first embodiment (the outcoupling section comprises only the plurality of curved outcoupling lines). Device 1 has a planar waveguide 2 with a thickness produced with known manufacturing tolerances in the range of some nanometers. A divergent beam of coherent light 61 is successively generated at different locations in a beam generation zone 612. The beam generation zone 612 is a circular shaped area arranged, for example, at the lower surface of the substrate 22 (as the first plane parallel to the outer surface of the waveguide), and has a size which depends on the manufacturing tolerances. For each successively generated beam of coherent light 61 that location in the detection zone 632 where a relative maximum intensity of the decoupled portion 63 of the diffracted coherent light occurs is determined. The relative maximum intensity is determined in that the decoupled portion 63 of diffracted coherent light 63 is detected (in a scanning manner) along a straight line 632 (as detection zone). This allows to determine for each generated divergent beam of coherent light 61 in the beam generation zone 612 that location on the straight line 632 where a relative maximum intensity of the decoupled portion 63 of the diffracted coherent light occurs. The second focal location 631 is then defined as being that location where the highest relative maximum intensity occurs. Finally that location in the beam generation zone 612 where the beam is generated resulting in the highest relative maximum intensity at the second focal location 631 is defined as the first focal location 611.

Detection only along a straight line 632 (and not in a detection zone being formed by an area) is possible for the configuration shown in FIG. 7 since small deviations in the propagation direction of the beam of coherent light 62 in the waveguide result in the same absolute maximum intensity at the second focal location 631. In principle, this method can be carried out vice versa, i.e. the decoupled portion 63 of the diffracted coherent light 63 is successively detected along the straight line 632 and for each of the successive detection locations, the divergent beam of coherent light 61 is generated at all locations in the entire beam generation zone 6 to allow for detecting the highest intensity at the second focal location 631.

In FIG. 8 a method for detecting the signal of highest intensity in the zone of second focal location 631 is described for the device 1 according to the third embodiment (the outcoupling section comprises the plurality of curved outcoupling lines and the plurality of straight lines—FIG. 5). The configuration is shown in a top view to provide a better illustration. As described above, the third embodiment is different in that additionally the condition for diffraction (Bragg condition) at the plurality of straight lines 42 is to be met. This additional requirement implies that only one single first focal location 611 and only one corresponding single second focal location 631 fulfil the conditions for the maximum coupling of coherent light into, within and out of the planar waveguide. Thus, the detection at the second focal location 631 is to be carried out in a detection zone 633 which is not a straight line (different to FIG. 7) but rather is an area. The divergent beam of coherent light 61 is successively generated at different locations in a beam generation zone 612. The beam generation zone 612 is a circular shaped area arranged, for example, at the lower surface of the substrate on which the planar waveguide is formed. For each successively generated beam of coherent light (not shown) that location in the detection zone 632 having the relative maximum intensity of the decoupled portion of the diffracted coherent light (not shown) is determined. A relative maximum intensity is determined by detecting the maximum intensity of the decoupled portion of the diffracted coherent light in a circular shaped area 633 (as detection zone). This allows to determine for each generated divergent beam of coherent light 61 that location in the circular shaped area having a relative maximum intensity of the decoupled portion of the diffracted coherent light. The second focal location 631 is defined at that location having the highest relative maximum intensity (in this embodiment only one location in the detection zone). Finally, that location in the beam generation zone 612 where the beam is generated resulting in the highest relative maximum intensity at the second focal location is defined as the first focal location 611.

Figure 9:
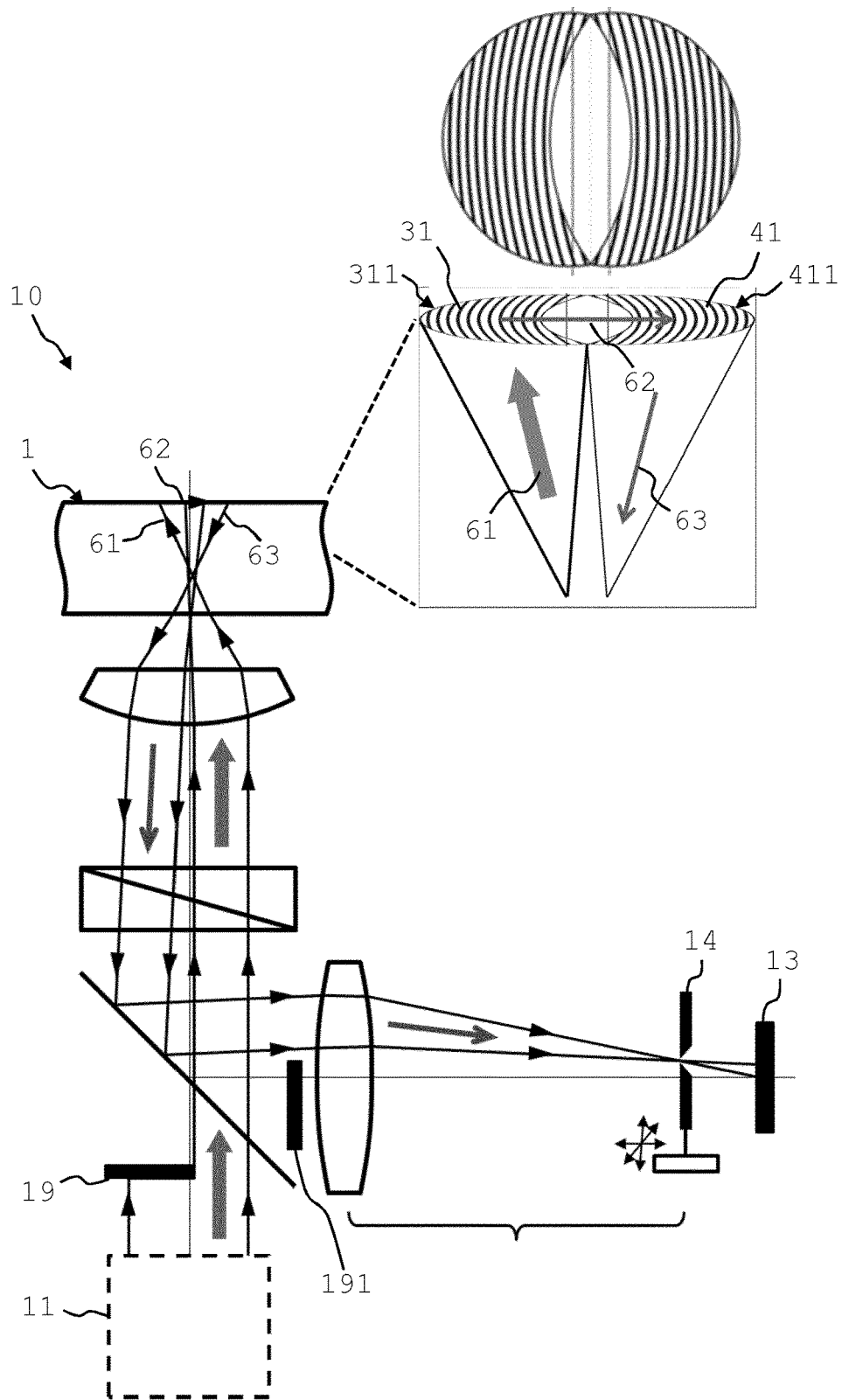
FIG. 9 shows the system of FIG. 6 comprising a first partial beam stop and a second partial beam stop.

FIG. 9 shows the system 10 which has in principle already been explained with reference to FIG. 6. However, structurally the system shown in FIG. 9 is different in that it comprises a first partial beam stop 19 and a second partial beam stop 191.

During use of the system 10, device 1 is used. In the present example device 1 has the incoupling lines 31 arranged in a partial first surface portion 311 and the curved outcoupling lines 41 arranged in a partial second surface portion 411. Partial first surface portion 311 and partial second surface portion 411 do not overlap so that the plurality of incoupling lines 31 and the plurality of curved outcoupling lines are arranged spatially separated. The target sample (not shown) is applied to the binding sites which are arranged in the present example along the curved outcoupling lines 41 (but could generally be arranged at the plurality of incoupling lines 31 as well).

During use of the device, similar to FIG. 6 the incoupling lines 31 couple divergent beam of coherent light 61 generated at the first focal location into the planar waveguide (not separately shown in the present illustration). The beam of coherent light coupled into the waveguide propagates as beam together with its evanescent field. A portion of the evanescent field (and thus of the beam propagating through the waveguide) is diffracted by the plurality of curved outcoupling lines 41 in a manner such that a decoupled portion of diffracted coherent light 63 converges into the second focal location to be detected as signal representative of the binding affinity between the binding sites and the target sample.

Advantageously, a first partial beam stop 19 restricts (i.e. by masking out) the beam of coherent light generated by laser light source 11. Hence, a restricted divergent beam of coherent light 61 illuminates only a first partial surface portion 311 which comprises the plurality of incoupling lines 31. In other words, first beam stop 19 restricts the coherent light in a manner such that only incoupling lines 31 are illuminated and no light propagates towards second partial surface portion 411 in which curved outcoupling lines 41 are arranged. This is particularly advantageous to attenuate background light by preventing the detection of reflected portions of coherent light.

Second beam stop 191 is arranged along the path of propagation of the decoupled portion 63 of coherent light in a manner to mask out light other than light diffracted at the curved outcoupling lines 41, which then propagates through diaphragm 14 to optical detector 13.

The invention claimed is:

1. A device for use in the detection of binding affinities, the device comprising a planar waveguide arranged on a substrate, the planar waveguide having an outer surface and a plurality of incoupling lines for coupling a beam of coherent light into the planar waveguide in a manner such that in operation a parallel beam of coherent light propagates along the planar waveguide with an evanescent field propagating along the outer surface thereof, wherein the plurality of incoupling lines are arranged at a first surface portion of the outer surface or the planner waveguide and are curved and arranged to have an increasing distance between adjacent incoupling lines when viewed in the direction of propagation of the parallel beam of coherent light along the planar waveguide, the arrangement of the plurality of incoupling lines and the distance between adjacent incoupling lines being such that in operation a divergent beam of coherent light of a predetermined wavelength coming from a predetermined first focal location and impinging on the plurality of incoupling lines is coupled into the planar waveguide in a manner such that the parallel beam of coherent light propagates along the planar waveguide, wherein a plurality of binding sites capable of binding a target sample is attached to the outer surface along at least one further plurality of lines arranged in an outcoupling section of the planar waveguide, the at least one further plurality of lines comprising a plurality of curved outcoupling lines which are arranged at a second portion of the outer surface of the planar waveguide and are arranged to have a decreasing distance between adjacent curved outcoupling lines when viewed in the direction of propagation of the coherent light impinging thereon so as to be capable of diffracting a portion of the coherent light of the predetermined wavelength impinging on the curved outcoupling lines to decouple it from the planar waveguide in a manner such that the decoupled portion of coherent light of the predetermined wavelength converges into a predetermined second focal location to provide at the second focal location a signal which, when compared to a known signal representative of the binding sites only, is representative of the binding affinity between the binding sites and the target sample, wherein the first surface portion includes a blank section in which there are no lines and wherein the second surface portion includes a further blank section in which there are no lines, the blank sections being formed to avoid a second order Bragg reflection.

2. The device according to claim 1, wherein the first surface portion and the second surface portion are arranged spatially separated at the outer surface of the planar waveguide.

3. The device according to claim 1, wherein the first surface portion and the second surface portion are arranged at the outer surface of the planar waveguide to at least partially overlap in a manner such that the blank section and the further blank section form a common blank section.

4. The device according to claim 1, wherein first surface portion and the second surface portion are of the same size.

5. The device according to claim 1, wherein the at least one further plurality of lines arranged in the outcoupling section further comprises a plurality of straight lines, the straight lines running parallel to one another with a constant distance between adjacent straight lines and being arranged at an angle ($\beta$) relative to the direction of propagation of the parallel beam of coherent light in a manner such that a portion of the parallel beam of coherent light is diffracted under a diffraction angle (α) relative to the straight lines such that the diffracted portion of the parallel beam of coherent light impinges onto the plurality of curved outcoupling lines, and wherein the attached binding sites are arranged along the plurality of straight lines or along the plurality of curved outcoupling lines.

6. The device according to claim 5, wherein the plurality of curved outcoupling lines is arranged at the outer surface in a partition of the planar waveguide through which the portion of the parallel beam of coherent light diffracted at the straight lines propagates, and through which no other light of the parallel beam of coherent light propagates.

7. The device according to claim 1, wherein a surface coating layer is arranged on top of the outer surface of the planar waveguide, the surface coating layer having a porous internal structure to allow target sample applied to the coating layer to diffuse therethrough to reach the binding sites attached to the outer surface of the planar waveguide.

8. A method for the detection of binding affinities, the method comprising the steps of:
   providing a device according to any one of the preceding claims,
   applying to the outcoupling section of the planar waveguide along the at least one further plurality of lines where the binding sites are arranged a target sample for which the binding affinity between the binding sites and the target sample is to be detected,
   generating at the predetermined first focal location a divergent beam of coherent light in a manner so as to impinge on the plurality of incoupling lines of the planar waveguide to couple the divergent beam of coherent light into the planar waveguide in a manner such that the beam of coherent light coupled into the planar waveguide propagates as a parallel beam of coherent light along the planar waveguide with an evanescent field of the parallel beam of coherent light propagating along the outer surface thereof, wherein a portion of the coherent light is diffracted by the plurality of curved outcoupling lines of the outcoupling section of the planar waveguide to decouple it from the planar waveguide in a manner such that the decoupled portion of the coherent light converges into the second predetermined focal location, and
   detecting the decoupled portion of coherent light at the second predetermined focal location to form a signal and comparing this formed signal with a known signal representative of the binding sites only to provide a signal representative of the binding affinity between the binding sites and the target sample.

9. The method according to claim 8, wherein the decoupled portion of coherent light is detected in a detection zone having a predetermined size and being arranged to include the second predetermined focal location to determine that location in the detection zone, where the decoupled portion of coherent light of the predetermined wavelength has a relative maximum intensity, and defining the location of the relative maximum intensity as the second predetermined focal location.

10. The method according to claim 9, wherein the divergent beam of coherent light is successively generated at different locations in a beam generation zone having a predetermined size and being arranged to include the first predetermined focal location, wherein for each successively generated beam of coherent light that location in the detection zone having the relative maximum intensity of the decoupled portion of coherent light is determined, defining that location in the detection zone where the relative maximum intensity is highest as the second predetermined focal location, and defining that location in the beam generation zone where the corresponding beam is generated as the first predetermined focal location.

11. The method according to claim 10, wherein the beam generation zone is an area in a first plane parallel to the outer surface of the planar waveguide, and wherein the detection zone is a straight line extending parallel to the direction of propagation of the parallel beam of coherent light in a second plane parallel to the outer surface of the planar waveguide.

12. The method according to claim 10, wherein the beam generation zone is an area in a first plane parallel to the outer surface of the planar waveguide, and wherein the detection zone is an area in a second plane parallel to the outer surface of the planar waveguide.

* * * * *